United States Patent
Burnes et al.

(10) Patent No.: US 7,027,871 B2
(45) Date of Patent: Apr. 11, 2006

(54) AGGREGATION OF DATA FROM EXTERNAL DATA SOURCES WITHIN AN IMPLANTABLE MEDICAL DEVICE

(75) Inventors: John E. Burnes, Andover, MN (US); Luc R. Mongeon, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 638 days.

(21) Appl. No.: 10/284,923

(22) Filed: Oct. 31, 2002

(65) Prior Publication Data

US 2004/0088027 A1    May 6, 2004

(51) Int. Cl.
*A61N 1/00*    (2006.01)
(52) U.S. Cl. .............................. 607/60; 607/59; 607/32
(58) Field of Classification Search ................. 607/32, 607/59, 60, 30; 128/903, 904
See application file for complete search history.

(56) References Cited

U.S. PATENT DOCUMENTS

| | | | | |
|---|---|---|---|---|
| 5,722,999 | A * | 3/1998 | Snell ............................. | 607/32 |
| 5,904,708 | A * | 5/1999 | Goedeke ....................... | 607/18 |
| 6,450,172 | B1 | 9/2002 | Hartlaub et al. ............. | 128/899 |
| 6,470,215 | B1 | 10/2002 | Kraus et al. .................. | 607/60 |
| 6,577,901 | B1 * | 6/2003 | Thompson .................... | 607/60 |
| 6,878,112 | B1 * | 4/2005 | Linberg et al. .............. | 600/300 |
| 6,922,592 | B1 * | 7/2005 | Thompson et al. ............ | 607/59 |
| 2001/0031997 | A1 | 10/2001 | Lee .............................. | 607/59 |
| 2001/0031998 | A1 | 10/2001 | Nelson et al. | |
| 2001/0037220 | A1 | 11/2001 | Merry et al. | |
| 2001/0039375 | A1 | 11/2001 | Lee et al. | |
| 2001/0047194 | A1 | 11/2001 | Thompson et al. | |
| 2001/0049544 | A1 | 12/2001 | Lee .............................. | 607/59 |
| 2002/0077841 | A1 | 6/2002 | Thompson | |

FOREIGN PATENT DOCUMENTS

WO    WO 01/47410    5/2001

* cited by examiner

Primary Examiner—Robert E. Pezzuto
Assistant Examiner—Brian T. Gedeon
(74) Attorney, Agent, or Firm—Daniel G. Chapik; Girma Wolde-Michael

(57) ABSTRACT

An implantable device is described that collects and aggregates data from non-implanted medical devices external from a body of a patient. The device may also collect and aggregate data from medical devices implanted within the body. The implantable device includes a wireless transceiver to acquire physiological data from the external medical devices, and a storage medium to store the physiological data. A processor retrieves the physiological data and communicates the physiological data to a remote patient management system. The device may collect the physiologic data from the various external data sources, possibly over an extended period of time, and stores the data for subsequent upload to a common patient management system. In addition, the implantable device may collect physiological data from other medical devices implanted within the patient. In this manner, the device provides a central point for collection and aggregation of physiological data relating to the patient.

34 Claims, 5 Drawing Sheets

AGGREGATION OF DATA FROM EXTERNAL DATA SOURCES WITHIN AN IMPLANTABLE MEDICAL DEVICE

TECHNICAL FIELD

The invention relates generally to medical devices and, more particularly, to collection of physiological data generated by the medical devices.

BACKGROUND

It is common to provide therapy and monitor a patient using a variety of medical devices. Moreover, these medical devices may be used at different times, and in a variety of locations. One or more medical devices may, for example, be used to provide medical treatment or monitor physiological conditions while the patient resides within his or her home or office. At other times, the patient may visit clinics or hospitals where different medical devices may be used. These disparate medical devices generate a wealth of physiological data relating to the symptoms and condition of the patient.

SUMMARY

In general, the invention is directed to an implantable data aggregation device that collects and aggregates physiological data for a patient from a variety of data sources. For example, the device collects physiological data from non-implanted medical devices external from a body of the patient. The device collects the physiological data from the various external data sources, possibly over an extended period of time, and stores the data for subsequent upload to a central patient management system. In addition, the implantable device may collect physiological data from other medical devices implanted within the patient. In this manner, the device provides a central point for collection and aggregation of physiological data relating to the patient.

In one embodiment, the invention is directed to a method comprising acquiring physiological data from a plurality of medical devices external to a body of a patient, and aggregating the physiological data within a device implanted within the body of the patient. The method further comprises communicating the aggregated physiological data from the implanted device to a remote system.

In another embodiment, the invention is directed to a method comprising receiving physiological data from a medical device external to a body of a patient, and storing the physiological data within a device implanted within the body of the patient.

In another embodiment, the invention is directed to an implantable device comprising a wireless transceiver to acquire physiological data from a medical device external to a body of a patient, and a storage medium to store the physiological data.

The techniques may offer one or more advances in the art. An implantable data aggregation device (IDAD), in accordance with the invention, may allow physiological data to be continuously collected and aggregated over extended periods of time, regardless of the location of the patient. For example, the IDAD may collect physiological data from other medical devices while the patient is located within his or her home, at his or her office, or undergoing tests at a clinic or hospital. Regardless, the IDAD collects information from the other medical devices to generate a comprehensive physiological profile for the patient.

The IDAD may communicate the aggregated physiological data to a central patient management system for access by a clinician. Consequently, the clinician need not access a number of disparate systems to view physiological data relating to the patient. Instead, the clinician may access the patient management system to view physiological data collected from numerous medical devices, which may be external medical devices, additional implanted medical devices, or combinations thereof. Thus, the techniques described herein may provide a more efficient mechanism for collection of extensive physiological data for the patient, and presentation of that data to a clinician by a common system. This may allow clinicians to more fully appreciate the current health of the patient, and more easily render accurate diagnosis and treatment of the patient via a single remote patient management system.

The details of one or more embodiments are set forth in the accompanying drawings and the description below. Other features, objects, and advantages will be apparent from the description and drawings, and from the claims.

DETAILED DESCRIPTION

Figure 1:
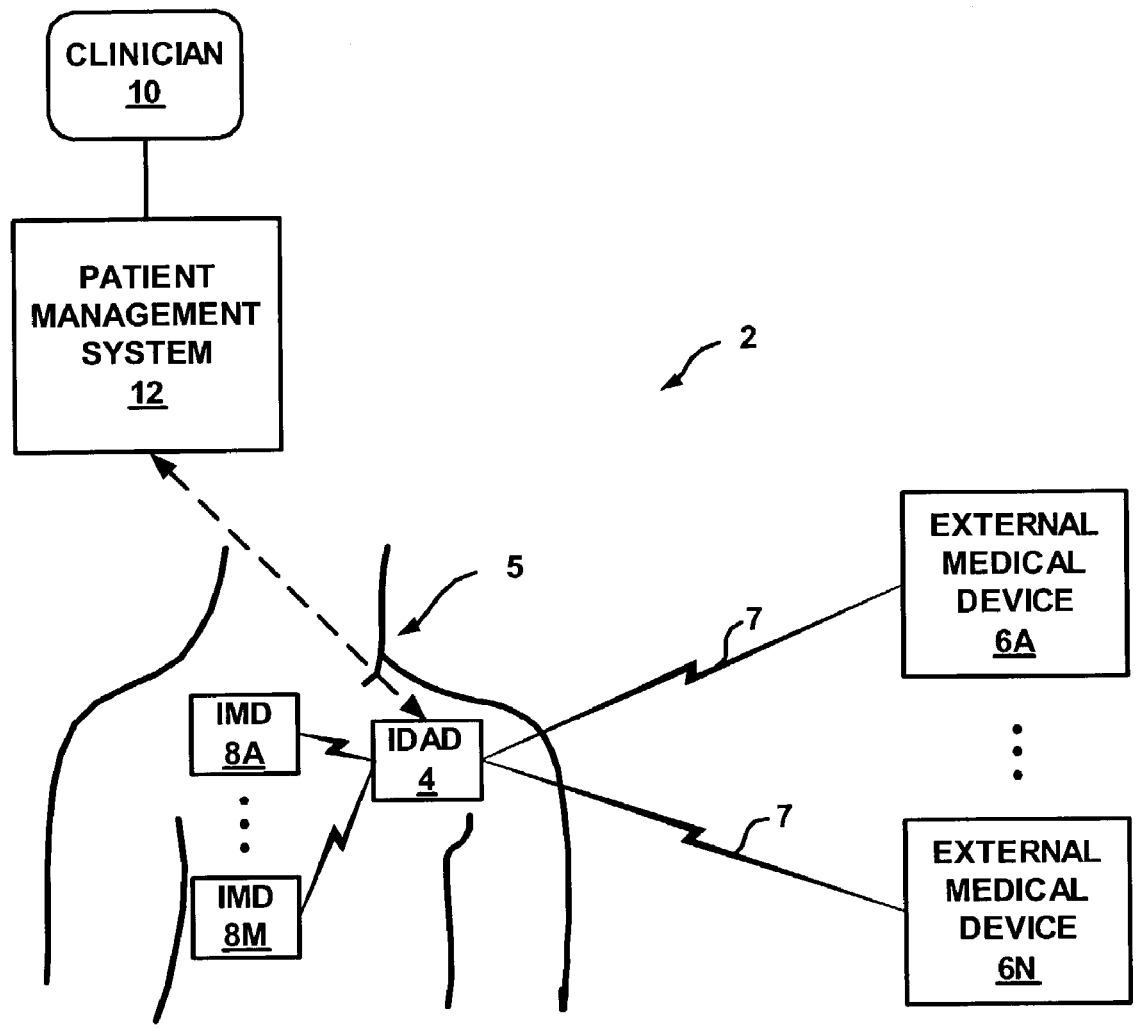
FIG. 1 illustrates an example system in which an implantable data aggregation device within a patient provides centralized collection and aggregation of physiological data from external and internal data sources.

FIG. 1 illustrates an example system 2 in which an implantable data aggregation device (IDAD) 4 within a patient 5 provides centralized collection and aggregation of physiological data from external and internal data sources. More specifically, IDAD 4 receives physiological data from external medical devices (EMDs) 6A–6N, implantable medical devices (IMDs) 8A–8M, or combinations thereof.

IDAD 4 may be an implantable device dedicated to the collection and aggregation of physiological data for patient 5. Alternatively, IDAD 4 may be an implantable medical device adapted for collection and storage of physiological data. Accordingly, IDAD 4 and IMDs 8 may take the form of a variety of implantable medical devices. One example of an implantable medical device is a pacemaker. Such a device typically includes at least one pacing and sensing lead for delivery of pacing pulses to a heart of patient 5. Another example of an implantable medical device is a pacemaker-cardioverter-defibrillator ("PCD"). Other examples include an implantable brain stimulator, an implantable gastric system stimulator, an implantable nerve stimulator or muscle stimulator, an implantable lower colon stimulator (e.g., in gracioplasty applications), an implantable drug or beneficial agent dispenser or pump, an implantable cardiac signal loop or other type of recorder or monitor, an implantable gene therapy delivery device, an implantable incontinence prevention or monitoring device, an implantable insulin pump or monitoring device, and so on. Thus, IDAD 4 may find wide application in conjunction with almost any appropriately adapted implantable medical device. IDAD 4 and/or IMDs 8 may continuously collect physiologic information about patient 5 including heart rate, heart rate variability, blood glucose levels, oxygen saturation, partial pressure of oxygen in the blood, blood pressure, baro-reflex measures, electrogram morphologies, lung wetness, and the like.

Similarly, EMDs 6 may be any of a variety of external medical devices that generate physiological data for patient 5. For example, EMDs 6 may include a variety of patient monitoring devices such as an external blood pressure monitor, an external heart rate monitor that measure heart rate and heart rate variability, a external blood glucose monitor, a scale that measures the weight of patient 5, an electronic questionnaire regarding patient symptoms or health status, a Holter monitor, an external EKG or ECG monitor, an external cardiac signal loop recorder, a temporary cardiac pacing system having an external pulse generator, and the like. Another example is a continuous positive airway pressure (CPAP) device or an oxygen delivery system that is often used with patients suffering from sleep apnea, pulmonary edema, or other disorders. Such as device may provide a CPAP therapy or respiratory status to IDAD 4 for aggregation with other physiological data for patient 5. In addition, EMDs 6 may include external drug delivery systems that may provide physiological data in the form of recent dosage levels, dosing history, and the like. Another example is an external device for testing the blood to provide a variety of information, such as prothrombin time, which may assist in titrating anti-coagulation medication or the current levels of B-type natriuretic peptide (BNP), which may aid the diagnosis and management of congestive heart failure (CHF). Additionally, EMDs 6 may include physiologic variables such as respiration rate, respiratory gases, blood pressure, heart rate, ECG and the like collected by an exercise machine (e.g. a treadmill, stair stepper, stationary bike, etc.) during exercise at home, in a clinician office, or in a gym. Similarly, data about a particular workout could be collected, including exercise times, workout level, calories burned, distances or speeds.

Consequently, EMDs 6 and IMDs 8 may provide a wealth of information related to the status and treatment of patient 5. In the event IDAD 4 is also a medical device, it may supplement the collected physiological data with physiological data measured directly by IDAD 4. In this manner, IDAD 4 provides a central point for collecting and aggregating physiological data relating to patient 5.

IDAD 4 communicates with EMDs 6 via signals 7 in accordance with one or more wireless communication techniques, such as conventional RF telemetry protocols used to communicate within implanted medical devices.

IDAD 4 may also communicate with EMDs 6 via other wireless communication protocols. One example protocol, commonly referred to as Bluetooth, uses short-range 2.4 GHz radio technology employed to transport data between devices. Other possible protocols include IEEE 802.11a, 802.11b, and 802.11g, which are designed for wireless networking. Yet another possible protocol is HomeRF, which was initially designed for wireless communications between devices and appliances within a home.

The use of IDAD 4 allows physiological data to be continuously collected and aggregated over extended periods of time, regardless of the location of patient 5. For example, IDAD 4 may collect physiological data from EMDs 6 while patient 5 is located within his or her home. IDAD 4 may collect physiological data, for example, while patient 5 is asleep. Similarly, IDAD 4 may collect data while patient 5 visits different clinics, possibly to see different clinicians for different medical purposes. IDAD 4 may, for example, collect physiological data while patient 5 is undergoing a treadmill test at one clinic, and then later while the patient is connected to a dialysis machine at a second clinic. Regardless, IDAD 4 collects information provided by the external data sources, e.g., EMDs 8 to aggregate comprehensive physiological data for patient 5.

IDAD 4 communicates the aggregated physiological data to a remote system or database, e.g., central patient management system 12, for accesses via a clinician 10. Consequently, clinician 10 need not access a number of disparate systems to view physiological data relating to patient 5. In other words, clinician 10 may access patient management system 12 to view physiological data collected from numerous medical devices, which may be external medical devices 6, additional implanted devices 8, or combinations thereof. Thus, the techniques described herein may provide a more efficient mechanism for collection of extensive physiological data for patient 5 from a variety of data sources, and presentation of that data to clinician by a common system. This may allow clinicians to more fully appreciate the current health of patient 5, and more easily render accurate diagnosis and treatment of the patient via the remote patient management system 12. Accordingly, the invention may promote physician efficiency and reduce patient care cost.

IDAD 4 may use a variety of criteria to determine when to initiate the transfer of the physiological data to patient management system. IDAD 4 may, for example, communicate the collected physiological data periodically, e.g., every twenty-four hours. Alternatively, IDAD 4 may initiate a data transfer when a threshold amount of data has been collected, based on the criticality of the data, based on the period of time elapsed since the data was acquired, or other suitable algorithms.

Upon viewing the aggregated data via patient management system 12, remote clinician 10 may issue IDAD 4 one or more commands. Specifically, by way of similar communications to those described above, IDAD 4 may transmit control signals to EMDs 6 and IMDs 8 in response to communications received from remote patient management system 12. In this manner, IDAD 4 may not only provide a central point of collection and aggregation of physiological data, but may provide a central point of control over external devices 6. An example might be the automatic adjustment of CPAP pressures to titrate sleep apnea treatment.

Figure 2:
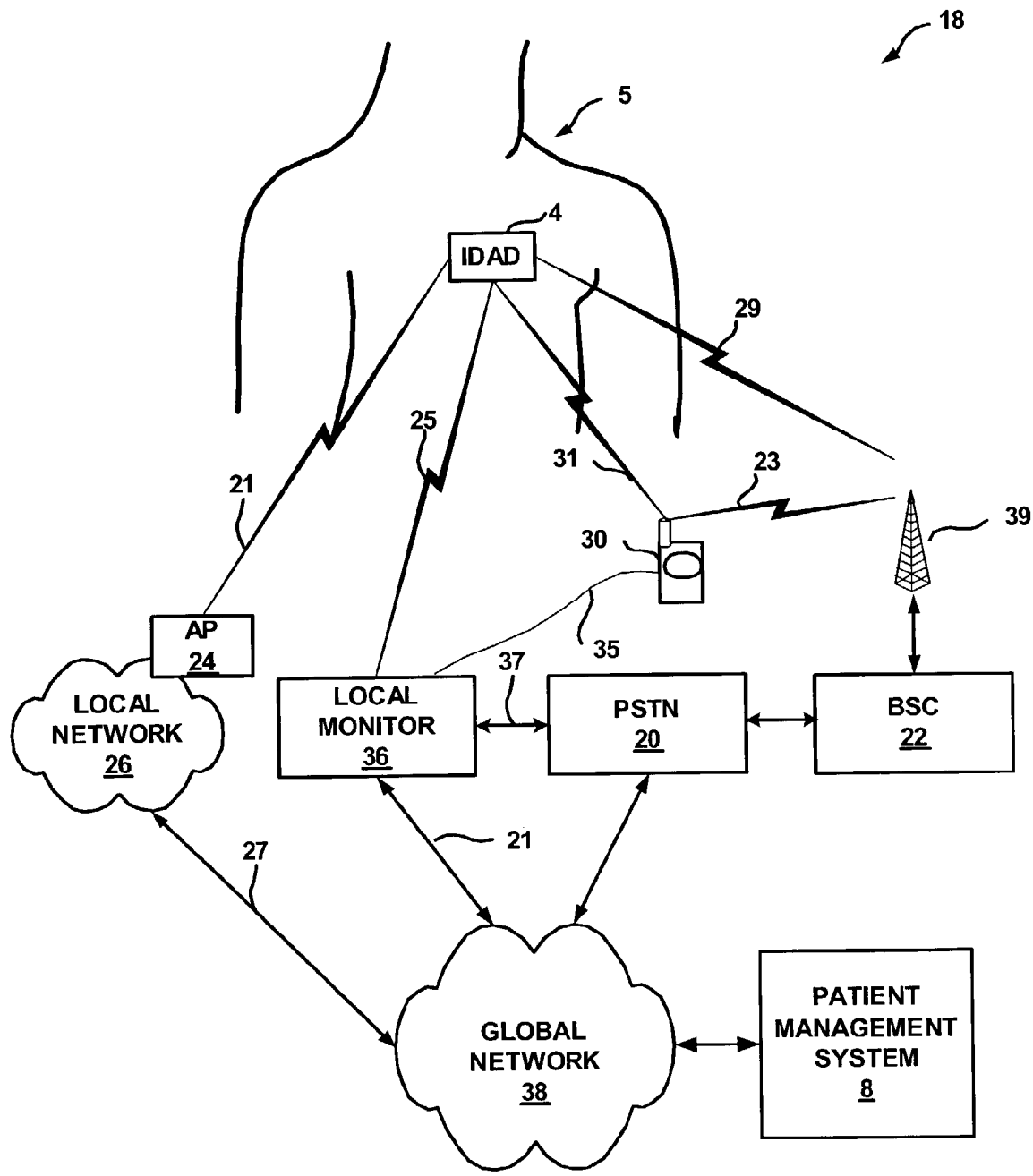
FIG. 2 illustrates the implantable data aggregation device in communication with a remote patient management system.

FIG. 2 illustrates a system 18 in which implantable data aggregation device (IDAD) 4 communicates with remote patient management system 12. IDAD 4 communicates with patient management system 12 via one or more communication channels. More specifically, IDAD 4 detects available channels for communicating with patient management system 12, and establishes communication sessions using one or more of the detected channels. IDAD 4 may select one or more of the detected communication channels based on a variety of criteria including the nature of the physiological data to be uploaded, the reliability of each detected channel, the speed of each detected channel, the cost for using each detected channel, and the like.

As one example, IDAD 4 may sense the availability of local monitor 36, which is typically located near patient 5 for providing access to patient management system 12. Local monitor 36 may be located, for example, within a home or office of patient 5, and may provide one or more wired communication channels for communicating with patient management system 12 via network 38. Local monitor 36 may upload the physiological data to patient management system 12, or may buffer the data for subsequent upload determined by a variety of factors, such as elapsed time since a previous upload, a current time of day, a manual trigger from patient 5, the amount of data received, a level of criticality of the data, and the like.

IDAD 4 attempts to establish a communication session 25 with local monitor 36 using a short-range wireless communication protocol. IDAD 4 may communicate with local monitor 36 in accordance with one or more wireless communication techniques, such as the RF telemetry protocols described above. For example, IDAD 4 and local monitor 36 may utilize conventional RF telemetry communication protocols, Bluetooth, IEEE 802.11a, 802.11b, and 802.11g, HomeRF, or other wireless communications.

Upon establishing a communication session with IDAD 4, local monitor 36 provides access to patient management system 12 via one or more channels. Local monitor 36 may, for example, provide a wired telephonic connection 37 to the public switched telephone network (PSTN) 20 for routing the communication to patient management system 12 via network 38. Connection 37 may, for example, comprises a modem for maintaining a dial-up connection using an analog phone line, and may provide relatively low-cost, low-speed access to network 38. Alternatively, or in addition, connection 37 may comprise a higher-speed communication channel to PSTN 20, such as an integrated services digital network (ISDN), a direct subscriber line (DSL), or the like.

In addition, local monitor 36 may provide a high-speed connection 21 directly to network 38. For example, local monitor 36 may make use of cable, optical, or other high-speed access medium for directly coupling IDAD 4 to network 38. Accordingly, local monitor 36 may include an Ethernet interface for receiving an Ethernet cable, a coaxial connector for receiving a cable line, and the like. Local monitor 36 may include routing functionality to support multiple patients 5, and may include firewall and other security applications to prevent unauthorized access of IDAD 4.

In addition, local monitor 36 may sense the availability of mobile telephone 30 via link 35, and whether cellular communications 23 may be established between mobile telephone 30 and base station 39. Alternatively, or in addition, IDAD 4 may have cellular functionality integrated within for establishing direct cellular communications 29 with base station 39. Cellular communications 23, 29 may take the form of any one of a number of conventional wireless communication techniques. One common technique is code division multiple access (CDMA) in which multiple communications are simultaneously conducted over a radio-frequency (RF) spectrum. Other examples include Global System for Mobile Communications (GSM), which uses narrowband time-division multiple access for communicating data, and General Packet Radio Service (GPRS). Base station controller (BSC) 22 provides an interface between base station 22 and the public switched telephone network (PSTN) 20 for routing the physiological data to patient management system 12 via network 38.

Furthermore, IDAD 4 may sense the availability of a wireless access point (AP) 24 for accessing a local network 26, such as a local area network at the home or office of patient 5. In particular, IDAD 4 may attempt to establish a communication session 21 with AP 24 located relatively near patient 5 using a wireless networking protocol. For example, IDAD 4 may attempt to establish communication session 21 using the IEEE 802.11a, 802.11b, 802.11g protocols, and the like, which are industry standard protocols for wireless LAN (WLAN) technology. In an 802.11b network, for example, two or more wireless nodes or stations establish communications in the 2.4 Gigahertz (GHz) frequency band. Many 802.11b networks contain at least one access point 24 that interfaces wireless and wired LANs. Example access points that are becoming prevalent are 3Com AirConnect 11 Mbps Wireless LAN Access Point, Lucent ORiNOCO AP-1000 11 Mbps Wireless Access Point, Cisco Aironet 4800 Access Point, and the Linksys Instant Wireless Network Access Point.

Local network 26 may be directly coupled to network 38 via a high-speed link 27, such as a T1 or a T3 data link. In this manner, IDAD 4 may establish communications with access point 24 to form a high-speed communication session with patient management system 12 via local network 26 and network 38.

IDAD 4 may be assigned a unique identifier, such as a local or global address according to the Internet Protocol (IP). Local monitor 36 or access point 24 may employ a network address translation (NAT) module to facilitate communications between IDAD 4 and patient management system 12. These devices may further include firewall and other security modules to prevent unauthorized access of IDAD 4.

Figure 3:
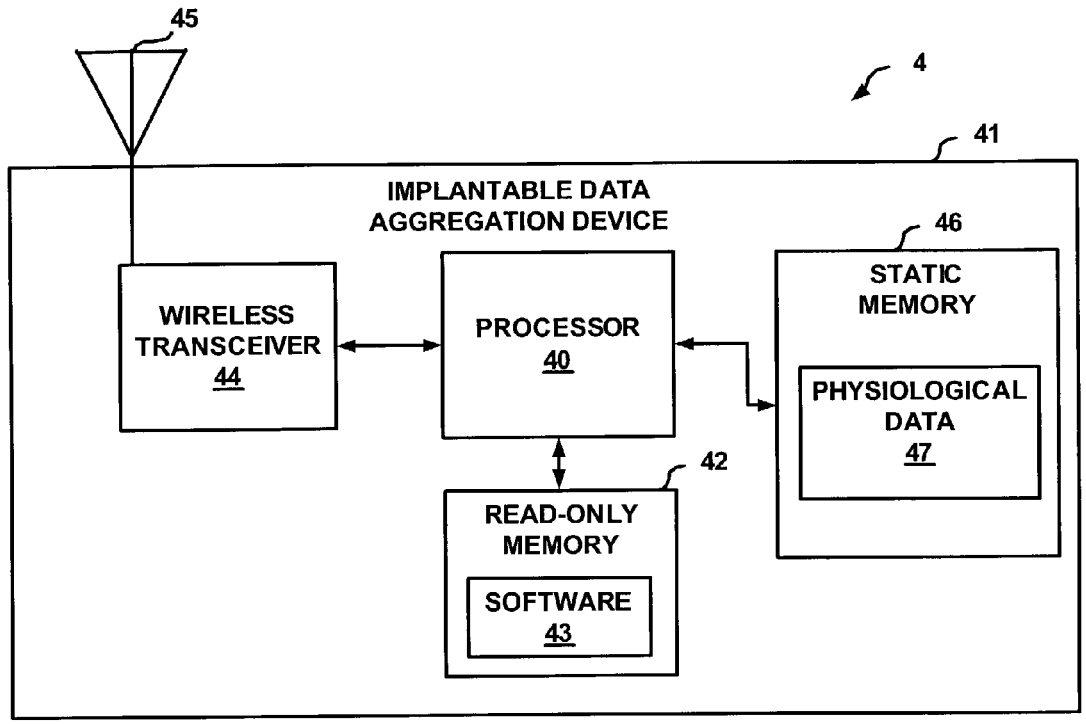
FIG. 3 is a block diagram illustrating an example embodiment of the implanted data aggregation device.

FIG. 3 is a block diagram illustrating an example embodiment of implanted data aggregation device (IDAD) 4. IDAD 4 includes hermetically sealed enclosure 41 that contains a processor 40, wireless transceiver 44, and memories 42, 46.

Processor 40 controls the operation of IDAD 4 by executing software instructions 43 stored within memory 42. Processor 40 may take one of a variety of forms including an embedded microprocessor, an embedded controller, a digital signal processor (DSP), and the like. Memory 42 may comprise any computer-readable medium suitable for storing instructions. Although illustrated as a read-only memory (ROM), memory 42 may take the form of random access memory (RAM), non-volatile random access memory (NVRAM), electrically erasable programmable read-only memory (EEPROM), flash memory, a miniaturized hard drive having a magnetic medium, and the like.

Wireless transceiver 44 receives and transmits radio frequency signals via antenna 45. In particular, processor 40 may make use of wireless transceiver 44 for communicating with IMDs 6, EMDs 8, local monitor 36 or access point (AP) 24 according to wireless communication protocols, as described above. IDAD 4 receives physiological data 47 from IMDs 6 and EMDs 8 via wireless transceiver 44, and stores the physiological data 47 within memory 46 for subsequent transmission to patient management system 12. Memory 46 may take the form of any static memory suitable for storing physiological data 47, such as non-volatile random access memory (NVRAM), flash memory, a miniaturized hard drive having a magnetic medium, and the like. The physiologic data 47 may be stored or cleared after download to patient management system 12.

Figure 4:
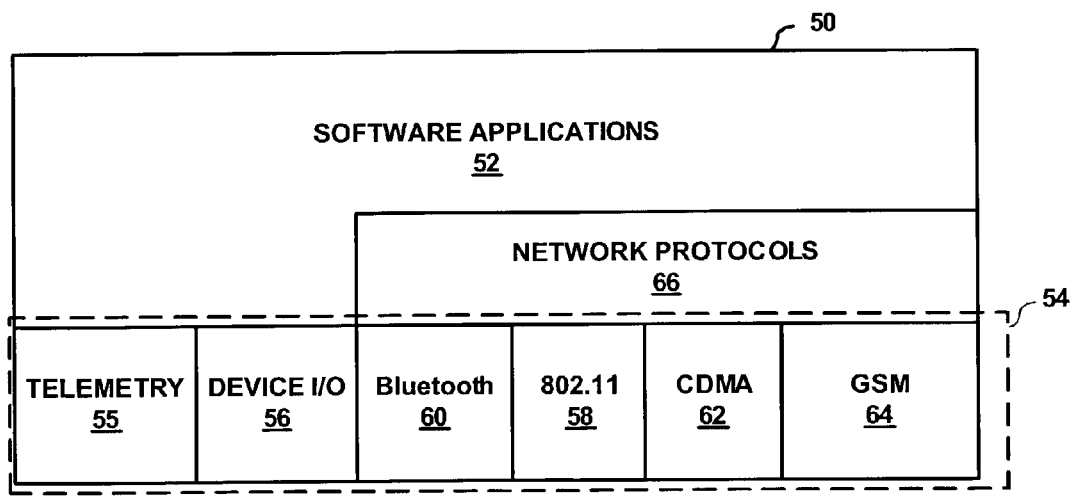
FIG. 4 is a block diagram illustrating an example software architecture for controlling operation of the implantable data aggregation device.

FIG. 4 is a block diagram illustrating an exemplary software architecture for controlling operation of IDAD 4. In general, the software architecture depicts a number of software modules for execution by processor 40. The software modules may include one or more high-level software applications 52 that carryout functions described herein. For example, software applications 52 may communicate with IMDs 6 and EMDs 8 to collect and aggregate physiological data 47 for patient 5. If IDAD 4 operates as an implantable medical device, software applications 52 may control other functions such as delivery of pacing pulses, drug delivery, patient monitoring, and the like. Software applications 52 make use of one or more drivers 54 that may be included within IDAD 4 to provide interfaces to a wide variety of hardware components. Drivers 54 may make use of corresponding chipsets and other hardware components incorporated within IDAD 4.

For example, IDAD 4 may include device I/O driver 56 may provide an interface to processor-controlled hardware, such as pacing circuitry, a drug delivery pump, and the like. Driver 55 provides an interface for communicating via protocols, such as conventional RF telemetry protocols. Driver 58 supports an 802.11 wireless communication protocol, such as 802.11a, 802.11b, or 802.11g. Similarly, driver 60 supports RF communications according to the Bluetooth protocol. IDAD 4 may also include driver 62, 64 for supporting cellular communications according to the code division multiple access (CDMA) protocol, or the Global System for Mobile Communications (GSM) protocol, respectfully. Software applications 52 may invoke network protocols 66 to make use of these drivers for communication with IMDs 6, EMDs 8, local monitor 36, and access point 24. Network protocols 66 may implement at TCP/IP network stack, for example, to support the Internet Protocol or other communication protocols. Other protocols may readily be incorporated within IDAD 4.

Figure 5:
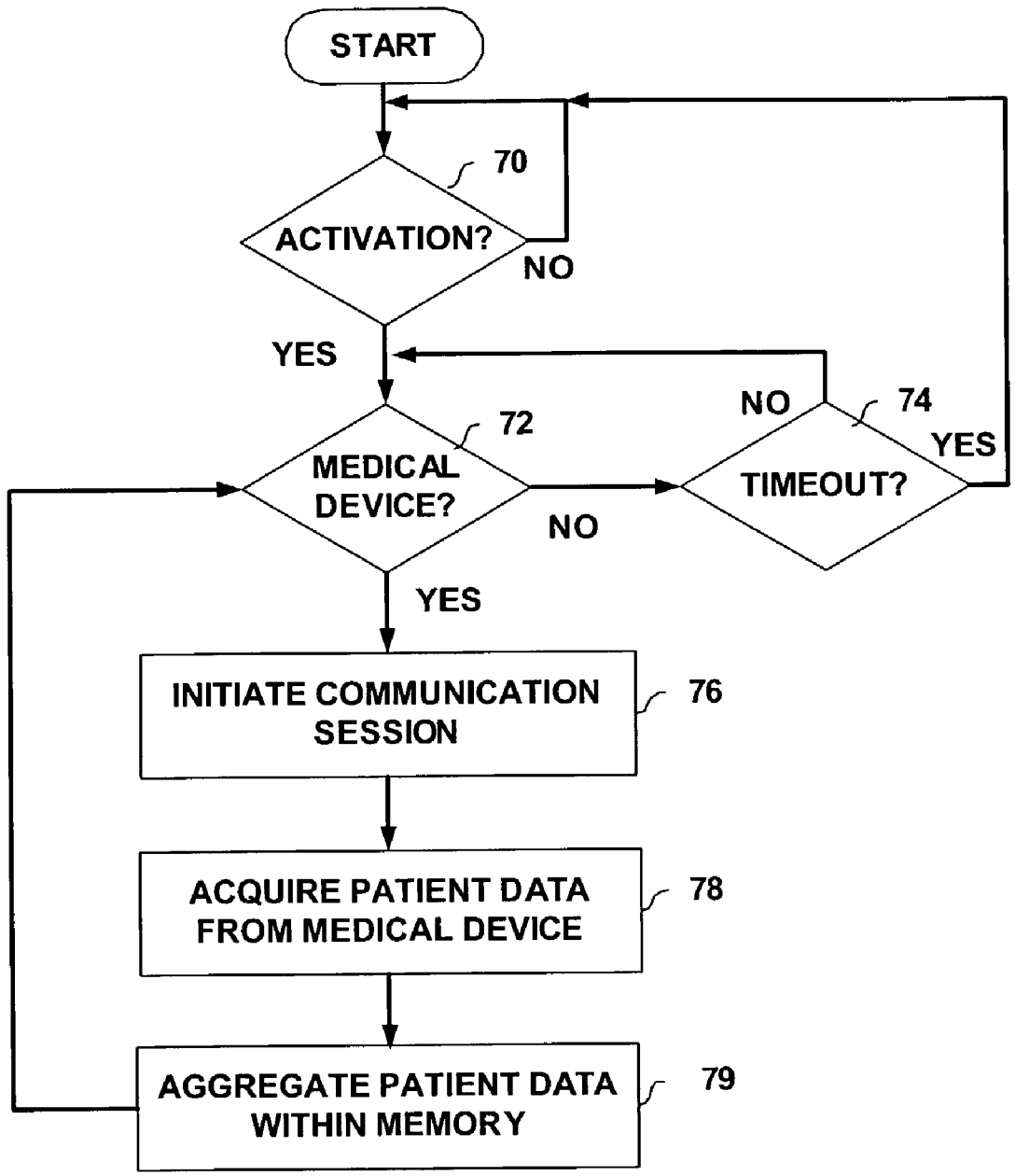
FIG. 5 is a flowchart illustrating example operation of the implantable data aggregation device when collecting and aggregating the physiological data for the patient.

FIG. 5 is a flowchart illustrating example operation of IDAD 4 when collecting and aggregating physiological data 47 for patient 5. Initially, IDAD 4 may be placed in a data acquisition mode with an external activation signal, e.g., by patient 5 or a clinician passing a magnet proximate the skin of the patient for activating the device (70). Another potential method for entering acquisition mode is through tapping of a pattern on the implanted device. Patient 5 or a clinician may, for example, place IDAD 4 into acquisition mode upon completing a test or other procedure with one of EMDs 6 during a visit to a hospital or clinic. As another example, patient 5 may place IDAD 4 in acquisition mode each morning to collect data from EMDs present within his or her home that may have been monitoring the patient while he or she slept. In this manner, patient 5 or a clinician may selectively activate IDAD 4 as needed to acquire data from internal and external medical devices 8,6.

Once activated, IDAD 4 begins sensing for EMDs 6, IMDs 8 using a variety of communication protocols, as described above (72). IDAD 4 may continue to sense for EMDs 6 and IMDs 8 for a period of time (74). If no devices are found, IDAD 4 terminates the acquisition mode, thereby conserving power.

If a medical device is detected, e.g., one of EMDs 6 or IMDs 8, IDAD 4 initiates a communication session with the detected device (76), and acquires physiological data 47 from the detected device (78). IDAD 4 receives the physiological data 47, and stores the data for subsequent transmission to patient management system 12 (79).

Figure 6:
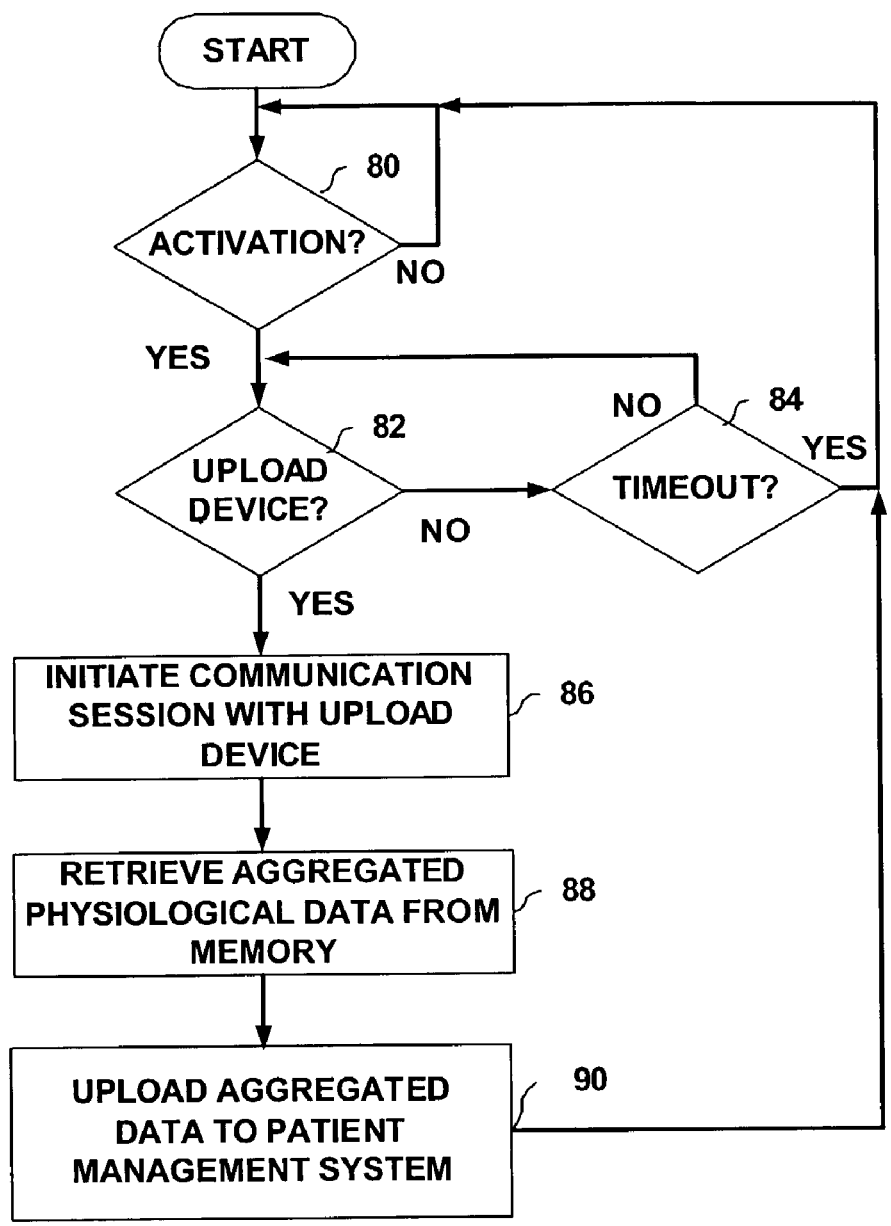
FIG. 6 is a flowchart further illustrating the operation of the implantable data aggregation device when transmitting the aggregated physiological data to the remote patient management system.

FIG. 6 is a flowchart further illustrating the operation of IDAD 4 when transmitting the aggregated physiological data 47 to patient management system 12. As described above in reference to FIG. 6, IDAD 4 may be activated by patient 5 or a clinician, e.g., by the patient or the clinician passing a magnet proximate the skin of the patient for activating the device (80). Upon activation, IDAD 4 not only senses for other medical devices, but senses for upload devices, e.g., access point 24, local monitor 36, or cell phone 30, for uploading any aggregated physiological data 47 stored within the device. In the case of embedded cell phone technology, IDAD 4 may directly initiate a cellular call for uploading the data.

Once activated, IDAD 4 begins sensing for upload devices for uploading the aggregated physiological data 47 using a variety of communication protocols, as described above (82). IDAD 4 may continue to sense for upload devices for a period of time (84). If no upload devices are found, IDAD 4 terminates the acquisition mode to conserve power.

If an upload device is detected, e.g., one of access point 24, local monitor 36, or cell phone 30 or other device, IDAD 4 initiates a communication session with the detected upload device (86), and retrieves the physiological data from memory 46 (88). IDAD 4 communicates the aggregated physiological data 47 to the detected device for patient management system 12 (90).

Various embodiments of the invention have been described. These and other embodiments are within the scope of the following claims.

What is claimed is:

1. A method comprising:
    acquiring physiological data from a plurality of medical devices external to a body of a patient;
    allocating a first memory location within an implanted medical device, wherein operation of the implanted medical device is unaffected by data residing within the first memory location;
    aggregating the physiological data within the first allocated memory location; and
    communicating the aggregated physiological data from the implanted device to a remote system.

2. The method of claim 1, further comprising presenting the aggregated physiological data from the remote system to a clinician.

3. The method of claim 1, wherein acquiring the physiological data by the implanted medical device comprises:
    entering a data acquisition mode in response to an activation signal;
    detecting the external medical devices upon entering the data acquisition mode; and
    acquiring the physiological data from the detected external medical devices.

4. The method of claim 3, wherein detecting the external medical devices comprises attempting to initiate wireless communication sessions with at least some of the external medical devices upon entering the data acquisition mode.

5. The method of claim 1, acquiring physiological data comprises receiving the physiological data from the external medical devices in accordance with one or more wireless communication protocols.

6. The method of claim 5, wherein the wireless communication protocols comprises at least one of Bluetooth, IEEE 802.11a, IEEE 802.11b, IEEE 802.11g and the HomeRF standard.

7. The method of claim 1, wherein communicating the aggregated physiological data to the remote system comprises establishing a cellular communication with the remote system.

8. The method of claim 1, wherein communicating the aggregated physiological data to the remote system comprises establishing a network communication session between the implantable medical device and a wireless access point.

9. The method of claim 1, further comprising:
    receiving additional physiological data from a medical device implanted within the body of the patient; and aggregating the additional physiological data received from the implanted medical device with the physiological data received from the external medical devices for communication to the remote system.

10. The method of claim 1, wherein communicating the aggregated physiological data from the implanted device to a remote system comprises:
   detecting an activation signal;
   detecting an communication interface of the remote system in response to the activation signal; and
   retrieving the aggregated physiological data from a computer-readable medium within the implanted device; and
   communicating the aggregated physiological data to the upload device for communication to the remote system.

11. The method of claim 10, wherein detecting the communication interface comprises attempting to initiate a communication session with the communication interface in accordance with a wireless communication device in response to the activation signal.

12. The method of claim 11, wherein the wireless communication protocols comprises at least one of BlueTooth, IEEE 802.11a, IEEE 802.11b, IEEE 802.11g, and the HomeRF standard.

13. A method comprising:
   providing a memory location within an implantable medical device for the collection, retention and transmission of physiological data from external medical devices wherein operation of the implantable medical device is unaffected by the physiolocical data;
   receiving physiological data from a medical device external to a body of a patient;
   storing the physiological data within the memory location; and
   communicating the physiological data from the memory location to an external device.

14. The method of claim 13, wherein the external device is one of a remote system and a database.

15. The method of claim 14, further comprising presenting the aggregated physiological data from the remote system to a clinician.

16. The method of claim 14, wherein communicating the aggregated physiological data to the remote system comprises communicating the aggregated physiological data to the remote system via one or more wireless communication protocols.

17. The method of claim 14, wherein communicating the aggregated physiological data to the remote system comprises establishing a cellular communication with the remote system.

18. The method of claim 14, further comprising:
   receiving commands from the remote system based on the aggregated physiological data; and
   delivering medical treatment to the patient via the implanted device in response to the commands.

19. The method of claim 14, further comprising:
   receiving commands from the remote system based on the aggregated physiological data; and
   forwarding the commands to the external medical device.

20. The method of claim 13, wherein receiving the physiological data comprises Initiating wireless communication sessions with the external medical device.

21. The method of claim 13, further comprising:
   receiving additional physiological data from a medical device implanted within the body of the patient; and
   storing the additional physiological data within the implanted device.

22. An implantable medical device comprising:
   a first memory location for providing data and instructions for operation of the implantable medical device;
   a second memory location allocated for collection of physiological data from external medical devices wherein operation of the implantable medical device is unaffected by the data stored within the second memory location that is provided by a storage medium; and
   a wireless transceiver to acquire the physiological data from the external medical device and transmit the physiological data.

23. The implantable device of claim 22, further comprising a processor to retrieve the physiological data and communicate the physiological data to a remote system.

24. The implantable device of claim 23, wherein the processor enters a data acquisition mode in response to an activation signal, and acquires the physiological data from the external medical device upon entering the data acquisition mode.

25. The implantable device of claim 23, wherein the processor initiates a wireless communication session with the external medical devices in accordance with a wireless communication protocol upon entering the data acquisition mode.

26. The implantable device of claim 23, wherein the wireless communication protocol comprises at least one of BlueTooth, IEEE 802.11a, IEEE 802.11b, IEEE 802.11g, and the HomeRF standard.

27. The implantable device of claim 23, wherein the processor establishes a cellular communication with the remote system.

28. The implantable device of claim 23, wherein the processor establishes a network communication session between the implantable medical device and a wireless access point.

29. The implantable device of claim 23, wherein the processor establishes a network communication session between the implantable medical device and a local monitor.

30. The implantable device of claim 23, wherein the processor receives additional physiological data from a second medical device implanted within the body of the patient, and stores the additional physiological data within the computer-readable medium for communication to the remote system.

31. The implantable device of claim 23, wherein the processor receives commands from the remote system based on the physiological data, and delivers medical treatment to the patient in response to the commands.

32. The implantable device of claim 23, wherein the processor receives commands from the remote system based on the aggregated physiological data, and forwards the commands to the external medical device.

33. The implantable device of claim 22, wherein the storage medium comprises one of a random access memory (RAM), a non-volatile random access memory (NVRAM), an electrically erasable programmable read-only memory (EEPROM), a flash memory, and a miniaturized hard drive having a magnetic medium.

34. The implantable device of claim 22, further comprising a hermetically sealed housing containing the wireless transceiver and the storage medium for implantation within the body of the patient.

* * * * *